United States Patent [19]

El Murr et al.

[11] Patent Number: 5,272,087
[45] Date of Patent: Dec. 21, 1993

[54] ENZYMATIC ELECTRODE AND ITS PREPARATION METHOD

[75] Inventors: Nabil El Murr, la Gacilly; Mohamed Slilam, Nantes, both of France

[73] Assignee: Centre National de la Recherche Scientifique (C.N.R.S.), Paris, France

[21] Appl. No.: 598,660

[22] PCT Filed: Apr. 19, 1989

[86] PCT No.: PCT/FR89/00182
§ 371 Date: Oct. 16, 1990
§ 102(e) Date: Oct. 16, 1990

[87] PCT Pub. No.: WO89/10395
PCT Pub. Date: Nov. 2, 1989

[30] Foreign Application Priority Data
Apr. 20, 1988 [FR] France .................. 88 05245

[51] Int. Cl.⁵ .............................................. C25B 11/12
[52] U.S. Cl. ...................................... 435/291; 435/817;
435/181; 435/177; 435/176; 435/288; 204/402;
204/403; 204/153.12
[58] Field of Search ............... 435/817, 14, 25, 288,
435/291, 176, 177, 180, 181, 311, 9; 204/403,
415, 418, 290 R, 153.12, 402,

[56] References Cited

U.S. PATENT DOCUMENTS

| | | | |
|---|---|---|---|
| 4,224,125 | 9/1980 | Nakamura et al. | 204/195 B |
| 4,321,123 | 3/1982 | Nakamura et al. | 204/195 B |
| 4,545,382 | 10/1985 | Higgins et al. | 204/403 |
| 4,576,704 | 3/1986 | Chiusole et al. | 204/402 |
| 4,595,479 | 6/1986 | Kimura et al. | 204/294 |
| 4,711,245 | 12/1987 | Higgins et al. | 435/25 |
| 4,820,399 | 4/1989 | Senda et al. | 204/403 |
| 4,857,167 | 8/1989 | Bashkin et al. | 204/403 |
| 4,957,593 | 9/1990 | Shaw et al. | 204/291 |
| 4,970,145 | 11/1990 | Bennotto et al. | 435/14 |

FOREIGN PATENT DOCUMENTS

| | | |
|---|---|---|
| 0177743 | 4/1986 | European Pat. Off. . |
| 2128620 | 5/1984 | United Kingdom . |
| 8910395 | 11/1989 | World Int. Prop. O. . |

OTHER PUBLICATIONS

"Magnetic Enzyme Membranes as Active Elements of Electrochemical Sensors, Specific Amino Acid Enzyme Electrodes" Calvot et al., FEBS Letters 59(2); 258–262; 1975.

Primary Examiner—Lyle A. Alexander
Attorney, Agent, or Firm—Jacobson, Price, Holman & Stern

[57] ABSTRACT

An enzymatic electrode, having a homogeneous composition throughout, consists essentially of a uniform intimate admixture of a conducting powder with at least one immobilized enzyme, or with an immobilized enzyme and a mediator agent or a co-enzyme, in a matrix. The electrode is one which has a surface available for direct contact with a substrate without a permeable or semi-permeable intermediate membrane or membranes. The enzymatic electrode is prepared, e.g., by intimately admixing (a) a homogeneous paste or matrix (resulting from an intimate admixture of a conducting powder with a binder), (b) at least one enzyme and (c) an enzyme crosslinking solution, and then incorporating therein a mediator agent and/or a co-enzyme.

20 Claims, 17 Drawing Sheets

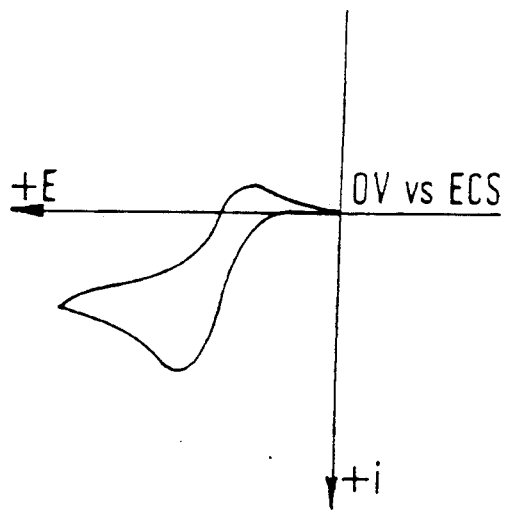
FIG. I(a)
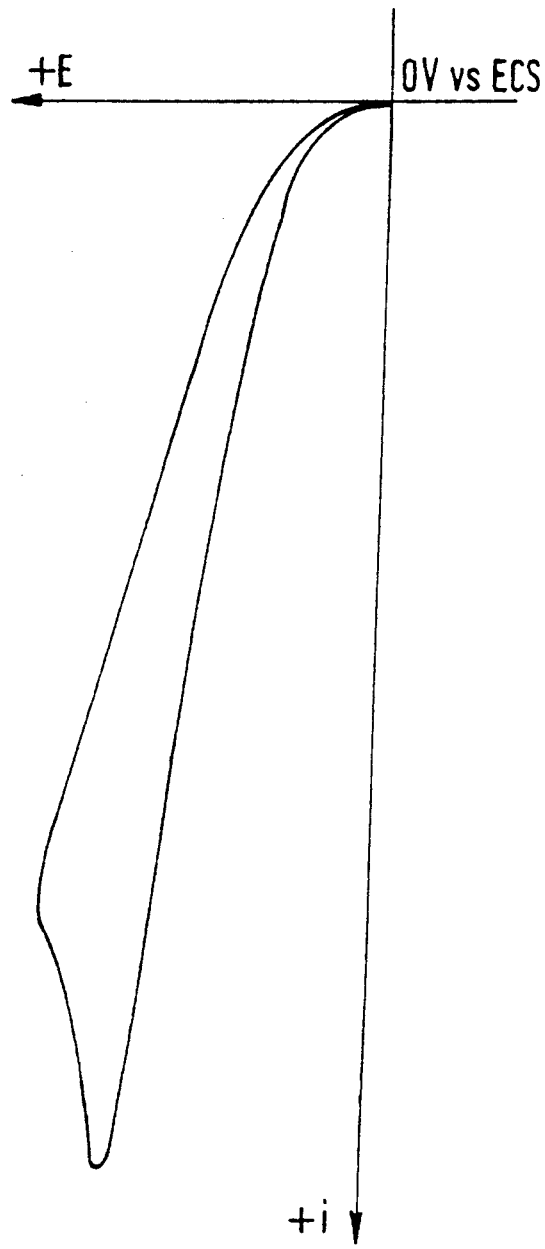
FIG. I(b)

−0.1V vs ECS

−0.1V vs ECS

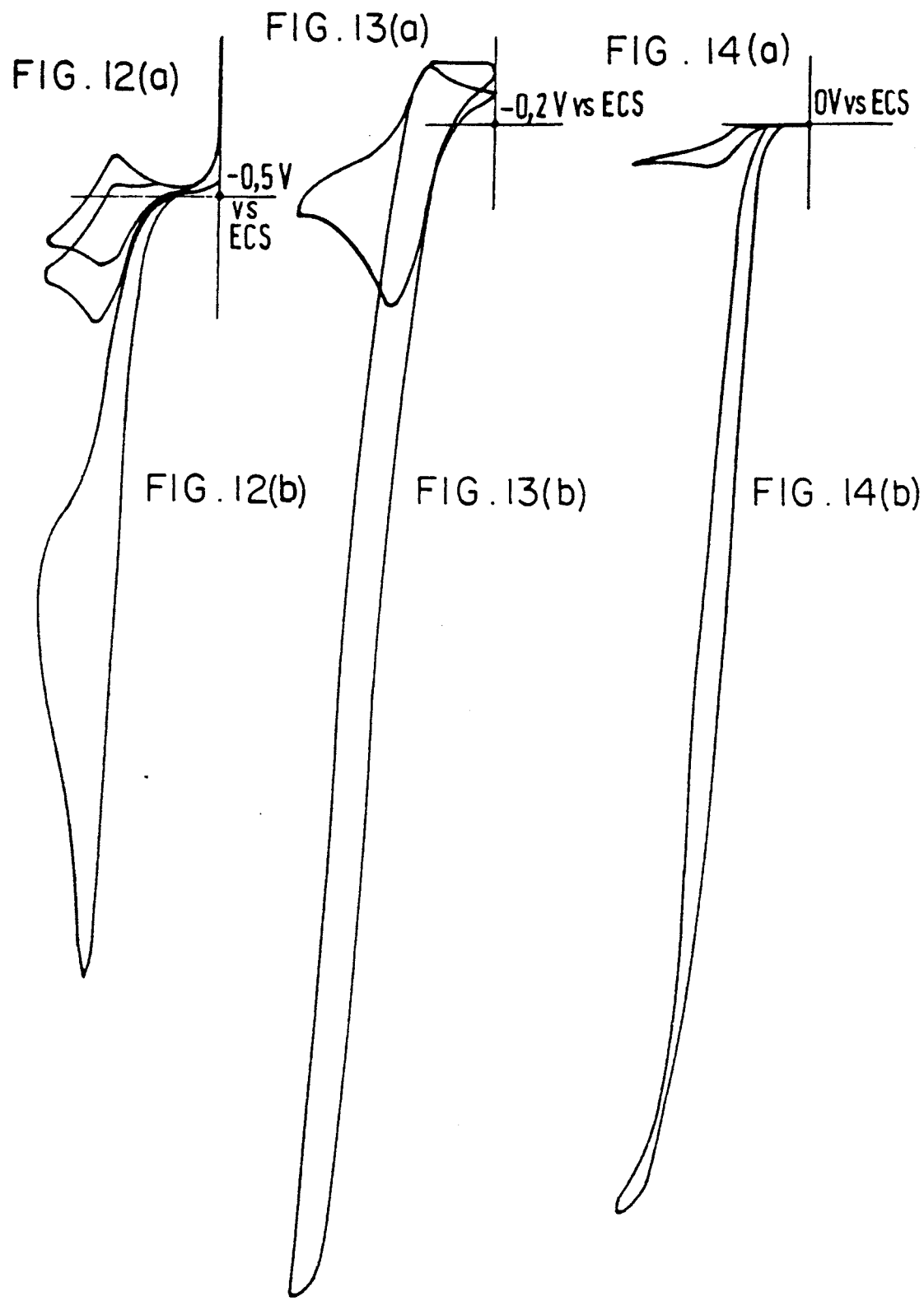

0V vs ECS 0V vs ECS

+0.2V vs ECS　　+0.2V vs ECS

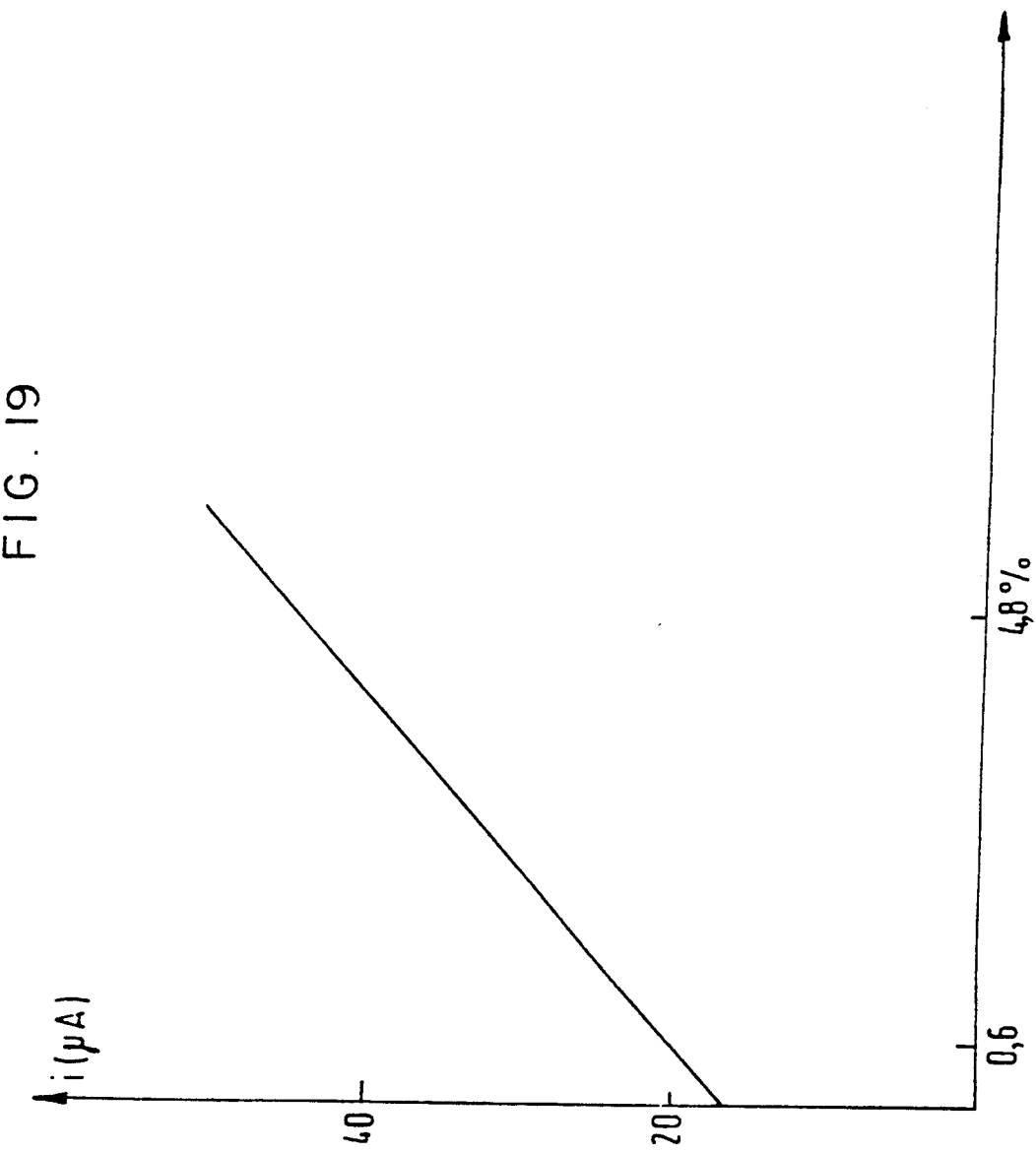

ENZYMATIC ELECTRODE AND ITS PREPARATION METHOD

The present invention was made at the Laboratoire R.M.N. et Réactivité Chimique (NMR and Chemical Reactivity Laboratory) at the University of Nantes, Centre National de la Recherche Scientifique (National Scientific Research Center) associate unit No. 472.

the present invention relates to an enzymatic electrode, in particular to an electrode having a surface which is renewable by friction or cutting, such that its useful surface area always remains the same, whatever the shape and the application of the electrode. The invention also applies to an enzymatic electrode of the disposable type. The invention also relates to the preparation of this electrode.

An enzyme electrode results from the combination of an electrochemical sensor and an enzyme, in particular in immobilized form. The functioning of an electrode of this type is based on the principle than an enzymatic degradation of the substrate to be determined is effected and that, in parallel, the appearance or the disappearance of one of the reaction products is measured.

Thus, in the case of the glucose electrode containing glucose oxidase as enzyme, the enzymatic reaction is as follows:

Several types of electrochemical detection can be envisaged, namely measurement of the disappearance of $O_2$, measurement of the appearance of $H^{30}$ ions and the anodic oxidation of $H_2O_2$ (platinum electrode) at a set potential and measurement of the resulting current.

Various techniques are known for immobilization of the enzymes, namely inclusion, according to which the enzyme is mechanically trapped in a polymer in the form of gel; crosslinking, according to which bifunctional chemical molecules, such as glutaraldehyde, permit crosslinking of enzyme molecules between one another or their co-crosslinking with inactive proteins, such as gelatin and albumin; confinement, according to which the enzyme is in solution inside a compartment separated from the solution to be determined by a porous membrane which allows the passage only of the small molecules; and covalent fixation which is effected by reaction between the functional groups carried by an activated surface and functional groups of the enzyme which do not participate in the catalytic activity of the latter.

Moreover, the dependence of the enzymatic reaction on the amount of oxygen dissolved in the solution can in some cases, in particular for determination in biological liquids, be a limiting factor for this determination technique. In fact, variations in the oxygen pressure can lead to significant fluctuations in the responses of the electrode; similarly, these responses are distorted if the amount of oxygen present becomes low. These disadvantages have led to the recommendation of the use of oxygen substitutes, in particular ferrocene and its derivatives, which are termed mediators. The reactions involved in this case are as follows in the case of the determination of glucose by means of a glucose oxidase GOD electrode using ferrocene as mediator:

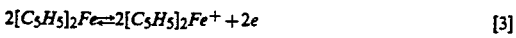

The electrochemical detection is the oxidation at the "naked" electrode of ferrocene to the ferricinium cation (reaction 3). Ferrocene can thus be introduced in a catalytic amount relative to the glucose and the current due to its electrochemical regeneration will serve as a glucose detection and determination signal.

This method has enabled satisfactory results to be obtained, but sometimes has the major drawback of introducing a substance which is foreign to the medium and which can prove toxic.

Conventionally, in enzymatic electrodes, the enzymes are kept near the surface of the electrode. This is the case in particular for the GOD electrode described by T. IKEDA et al. in Agric. Biol. Chem. 49(29), 541–543, 1985 and in Agric. Biol. Chem. 50(4), 883–890, 1986, the surface of the GOD-loaded electrode being covered by a film of nitrocellulose (cf. European patent application EP-A-177,743). In the publication "Analytical Sciences Dec. 1985, vol. 1", pages 455–457, IKEDA et al. describe a GOD electrode in which the GOD layer, applied on the electrode, is covered by a dialysis membrane, a mini-grating of gold and a "Nylon" net.

It is thus found that, according to the earlier technique for fixation of the enzyme at the surface of the electrode, it is necessary to protect the enzyme by a "cover" permeable to the solution and not to the enzyme. It has also been proposed to fix the enzyme on a chemical support.

The abovementioned enzymatic electrodes permit several specific determinations to be carried out, but they are frequently delicate in use because they demand a meticulous preparation before each measurement and they saturate fairly rapidly.

Moreover, the surface of the electrode can spoil easily and a loss of signal and a reduction in the reproducibility result. In fact, the surface is not renewable except by carrying out a regeneration treatment each time. Moreover, in the case of the fixation of enzymes by chemical reaction, in particular for the fixation of several different enzymes at the surface of the electrode, interferences or competitions can be produced which often render the preparation of the electrode uncontrollable.

According to the invention it is proposed to imprison the enzymes in a conductive matrix. For the analyses, this matrix is advantageously contained in an inert sheath, made of an insulating material, for example made of glass or plastic material, from which it protrudes at one end to comprise the useful surface. Before a measurement it suffices, if this proves necessary, to clean the electrode briefly, for example by simple rubbing on a piece of paper, which removes the used surface layer to a depth of a few angstroms; the electrode, the surface of which has been regenerated in this way, is then immersed in the liquid medium to be analyzed.

The electrode of the invention is easy to prepare, at very low cost, it can keep easily, it is always ready for use and it is very easy to handle and provides reproducible results. Without disadvantage it can contain a multi-enzyme system, as well as an electron mediator and/or a coenzyme. It can also be for once-only use and disposable.

The enzymatic electrode according to the invention is therefore characterized in that its enzymatic part and its detection part are combined, said electrode comprising a matrix made from a conducting powder providing for the detection and containing, intimately mixed with said powder, at least one immobilized enzyme incorporated homogeneously into its mass, said electrode being directly in contact with the substrate to be determined, without permeable or semi-permeable intermediate membrane or membranes.

In FEBS Letters Vol. 59, No. 2, Nov. 1975, C. Calvot et al. describe the production of a membrane by mixing lysine decarboxylase with a solution containing plasmatic albumin and glutaraldehyde, adding particles of magnetic iron oxide, casting the suspension on a plate to obtain a membrane of homogeneous thickness, crosslinking for 2 hours at ambient temperature and separating of the film formed. This film is fixed (by a magnet, which explains the presence of magnetic iron oxide particles in the membrane) on a $pCO_2$ electrode on which the presence of a porous sheet and of a membrane permeable to gas can be established. Thus, with this known electrode, an enzymatic reaction is produced at the film, followed by a diffusion of carbon dioxide and then a detection at the electrode. The enzymatic part and the detection part are therefore independent. The original concept on which the present invention is based is to have combined these two traditional parts of the electrode, which enables all of the disadvantages presented by the latter to be overcome straight-away. The separation existing in the known structures between the enzymatic part and the detection part presents problems of permeability and therefore of diffusion and detection, the diffusion kinetics affecting the reproducibility of the signal. Moreover, the use of an enzymatic membrane involves difficulties associated with the production of membranes to be applied to the detector body which are of constant thickness to ensure the correct diffusion of the products. Finally, with a membrane it is difficult to ensure a composition which is constant over time, and this has an adverse influence on the repetitive character of the measurements.

The separation of the enzymatic and detection parts is also observed in the enzymatic electrodes described in U.S. Pat. No. US-A-4,224,125 and in European patent application EP-A-177,743.

Any enzyme capable of entering into reaction with the substrate to be analyzed and/or with any other substance capable of providing an electrical signal representative of said substrate to be analyzed may be used as the enzyme in the electrode according to the invention.

The enzymes most commonly used are, more particularly, the oxidoreductases, which then involve the use of an agent, termed a mediator, for the transfer of electrons. The origin of the enzyme is not at all critical, because the electrode of the invention makes use only of its property of having a reaction which is directly or indirectly detectable by electrochemical means.

It is also possible to use, conjointly with a given enzyme, its co-enzyme, which is itself detectable by electrochemical means. This is the case, for example, for various dehydrogenases.

The amount of enzyme present in the conducting matrix can vary within wide limits, as a function of the inherent activity of each enzyme. The higher the activity of the enzyme, the lower the amount by weight of the enzyme in the matrix, it being pointed out that excessive proportions of enzyme do not interfere with the measurement strictly speaking, but are needlessly expensive. However, it goes without saying that the minimum amount of enzyme must be such that it provides a measurement signal which can be utilized in practice. For example, for the glucose oxidase (GOD) electrode the proportions can vary from 0.4 to 15% by weight with an enzyme of IU =200, and more particularly from 1 to 5% by weight.

The particle size distribution of the conducting powder is not critical; good results have been obtained with a powder having a particle size distribution of between 1 $\mu$m and 25 m, for example 5 $\mu$m on average.

The conducting powder is chosen, in particular, from carbon powders or graphite powders.

Preferably, the matrix is formed by mixing the powder with a binder which is inert, that is to say does not react in the voltage range under consideration, and used in particular in an amount of 10 to 40% by weight relative to the pasty conducting matrix thus obtained. The binder is advantageously a hydrophobic binder; paraffin oil, alpha-bromonaphthalene and silicone oil have given good results. For the choice of binder, reference may be made to R.N. ADAMS, in "Electrochemisty at solid electrodes", Ed. Marcel DEKKER, N.Y., 1969. In some cases, the binder is not indispensable, for example if the carbon powder is in a state in which it can form a matrix.

The amount of binder is chosen such that the matrix is not too fluid because of excess binder and, conversely, that it does not become because of lack of binder.

Moreover, the enzyme is immobilized inside the matrix of conducting material by means of at least one crosslinking agent or by means of physical imprisonment in the constituent matrix of the electrode, for example carbon. A crosslinking agent which may be mentioned is glutaraldehyde.

According to the invention, it is also possible to provide for the matrix of conducting material to contain, in addition, at least one mediator agent in an amount of from 0.01 to 3% by weight, in particular of from 0.05 to 1% by weight, relative to said matrix, this mediator being chosen, in particular, from ferrocene, nickelocene and their derivatives, as well as benzoquinone and other electron transfer agents.

By way of illustration, the ferrocene derivatives described by way of mediators in solution by A.E.G. GASS et al. in "Anal. Chem." 1984, 56, 667–671, may be incorporated in the matrix of the invention.

The matrix of the electrode according to the invention may also contain at least one co-enzyme.

To prepare the enzymatic electrode according to the invention, in a first embodiment the following are intimately mixed:
homogeneous paste or matrix resulting from intimate mixing of a conducting powder with a binder;
at least one enzyme; and
an enzyme crosslinking solution;
and in a second embodiment a conducting powder, capable of forming a matrix, and at least one enzyme are intimately mixed and this mixture is subjected to mechanical forces, in particular compression, in order to obtain a solid matrix physically imprisoning the enzyme.

In the two cases a mediator and/or a co-enzyme may be incorporated in the paste or matrix or the mixture.

In the case where the paste or matrix or the mixture contain (sic) a mediator, a fraction of conducting powder containing the mediator in a homogeneous fashion may be prepared by mixing said mediator in organic solution with the conducting powder and then evaporating off the solvent, and this fraction is mixed with the conducting matrix containing the enzyme.

For the determinations, the circuit using the electrode of the invention is a conventional circuit, one of the ends of the electrode being brought into contact with the solution in the measurement cell and the other with the electrical circuit of the potentiostat.

The enzymatic electrode according to the invention can assume various forms, inter alia a portable form for repeat use or for once-only use.

BRIEF DESCRIPTION OF THE DRAWINGS

The invention will be illustrated, without being in any way limited, by the description which follows, which is given with reference to the appended drawings and to the following examples, in which the percentages are given by weight unless indicated to the contrary:

FIGS. 1 to 19 are diagrams showing the results of determinations and measurements carried out with electrodes according to the invention.

Figure 20:
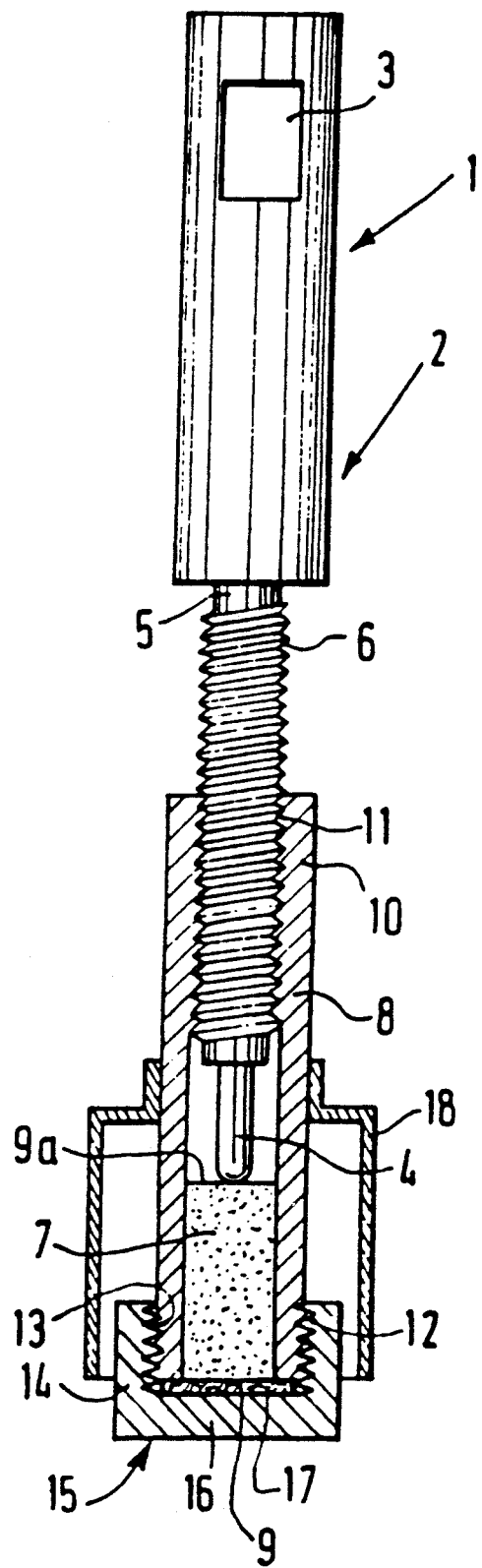
FIG. 20 illustrates schematically an electrode according to one embodiment of the invention, this electrode having a tubular general shape.

The electrode 1 is shown schematically in FIG. 20. It comprises an electrode holder 2, at one end of which a reading window 3 is arranged and which terminates at the other end in a contact 4. In the vicinity of this contact, the electrode holder has a smaller diameter, this part 5 of smaller diameter carrying a thread 6. The matrix 7 according to the invention containing the enzyme is placed in a cylindrical sheath 8 in such a way that is protrudes at one of the ends from said sheath 8 to form the useful surface 9 of the electrode. At the opposite end, the sheath 8 extends beyond the matrix 7 to form a part 10 carrying a thread 11 intended to cooperate with the thread 6 of the electrode holder 2, the contact 4 bearing constantly on the face 9a of the matrix 7 opposite to the surface 9.

Moreover, in the vicinity of its edge associated with this surface 9, the sheath 8 has an external thread 12 intended to cooperate with the screw thread 13 of the peripheral skirt 14 of a cap 15, on the bottom 16 of which a pallet 17 of filter paper or felt or analogous material is applied. An auxiliary and/or reference electrode 18 is associated with the enzymatic electrode 7.

For use, the cap is unscrewed. After each use, the cap 15 is replaced and, in order to regenerate the useful surface 9, the electrode holder 2 can be turned slightly, this ensuring friction of this surface 9 against the pallet 17.

EXAMPLE 1

Determination of glucose with the aid of a carbon paste electrode containing glucose oxidase, in the presence of ferrocene monocarboxylic acid as mediator, in the analysis medium.

(a) Preparation of the electrode 1 g of a carbon powder having a particle size distribution of average value 5 μm (Carbone Lorraine) and 0.36 ml of paraffin oil are mixed until a homogeneous paste is obtained.

300 mg of the carbon paste thus obtained are mixed intimately with 0.3 ml of a crosslinking solution having the following formulation:

| | |
|---|---|
| 2.5% glutaraldehyde | 25% |
| 15% bovine albumin | 29% |
| Phosphate buffer solution of pH 6.8 | 56% | and with the chosen amount of glucose oxidase. The mixture thus obtained is left in the mortar, at 4° C., for 10 to 30 minutes. It is scratched to obtain a sort of powder, which is taken up in 0.06 ml of paraffin oil.

(b) Glucose determination

This determination is carried out in the presence of ferrocene monocarboxylic acid as mediator, the reactions involved being analogous to those indicated in the preamble of the present description for ferrocene.

The analysis medium is a phosphate buffer medium of pH 8-9.

FIG. 1(a) shows the shape of the signal obtained by cyclic voltammetry with this electrode when ferrocene monocarboxylic acid is on its own in solution. The curve i=f(E) thus obtained corresponds to the oxidation of said acid to the corresponding ferroceric cation.

FIG. 1(b) is obtained when glucose is added to the above solution. An increase in the oxidation current is observed in the presence of glucose.

It must be pointed out that no current is detected at this potential with the electrode when the mediator is absent from the solution, even if the solution contains glucose.

Figure 2:
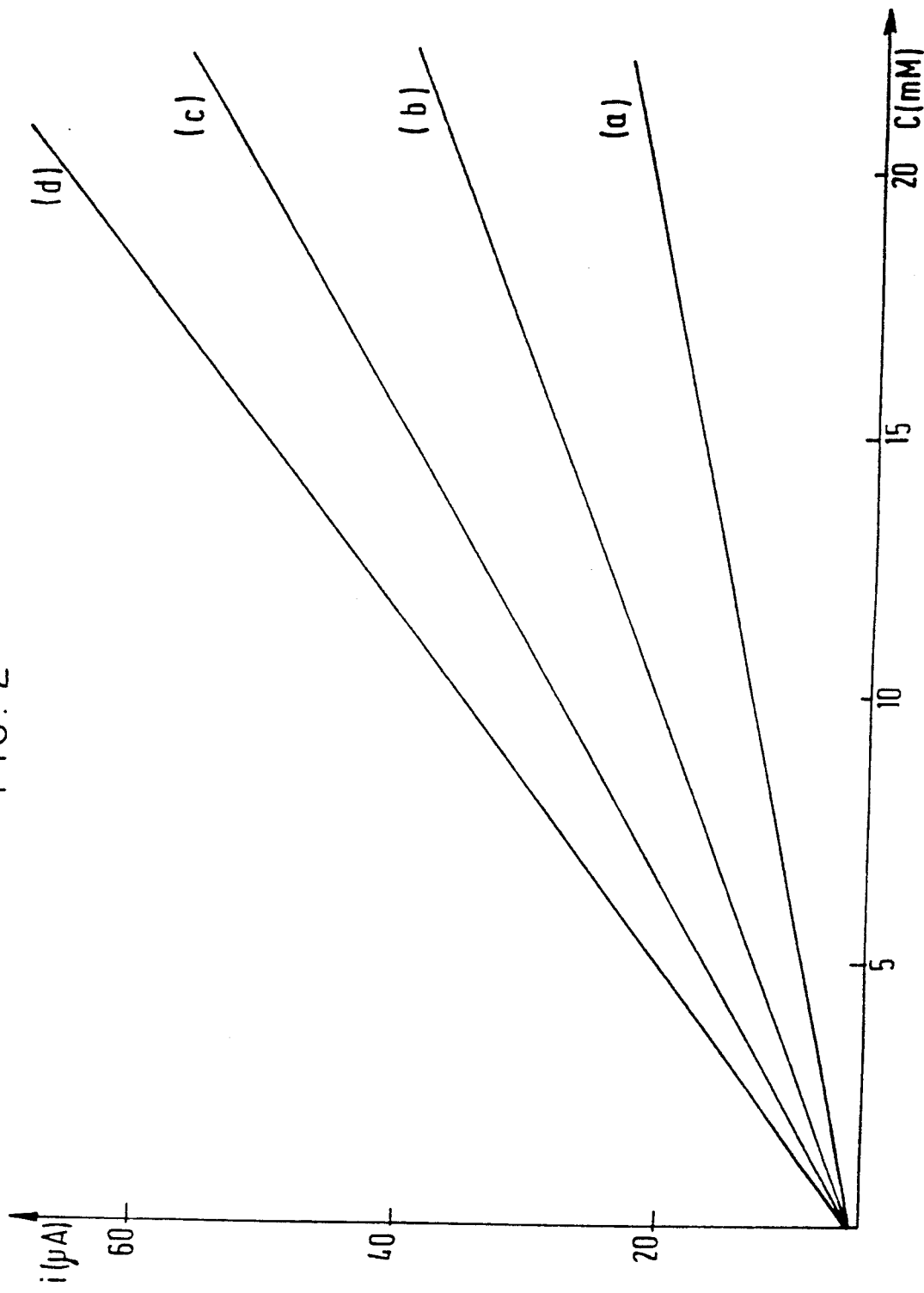

In FIG. 2 the response curves i=f(C) of this electrode as a function of the glucose concentration have been plotted for various GOD concentrations in the carbon paste of the electrode, under the following conditions:

mediator concentration in the analysis medium: $0.5 \times 10^{-3} M$ pH: 8.9 scanning speed: 2 mV/s

| Legend for FIG. 2 | |
|---|---|
| Abscissas: glucose concentration in mM | |
| Ordinates: current intensity in μA | |
| Curve | Number of units of GOD × 10⁻³ per gram of carbon paste |
| (a) | 1.4 |
| (b) | 2.8 |
| (c) | 4.3 |
| (d) | 5.8 |

FIG. 2 shows the straight line response of the electrode as a function of the glucose concentration. The four straight lines of this figure show that the higher the GOD concentration in the electrode paste the greater is the signal, that is to say the more sensitive is the detection.

Figure 3:
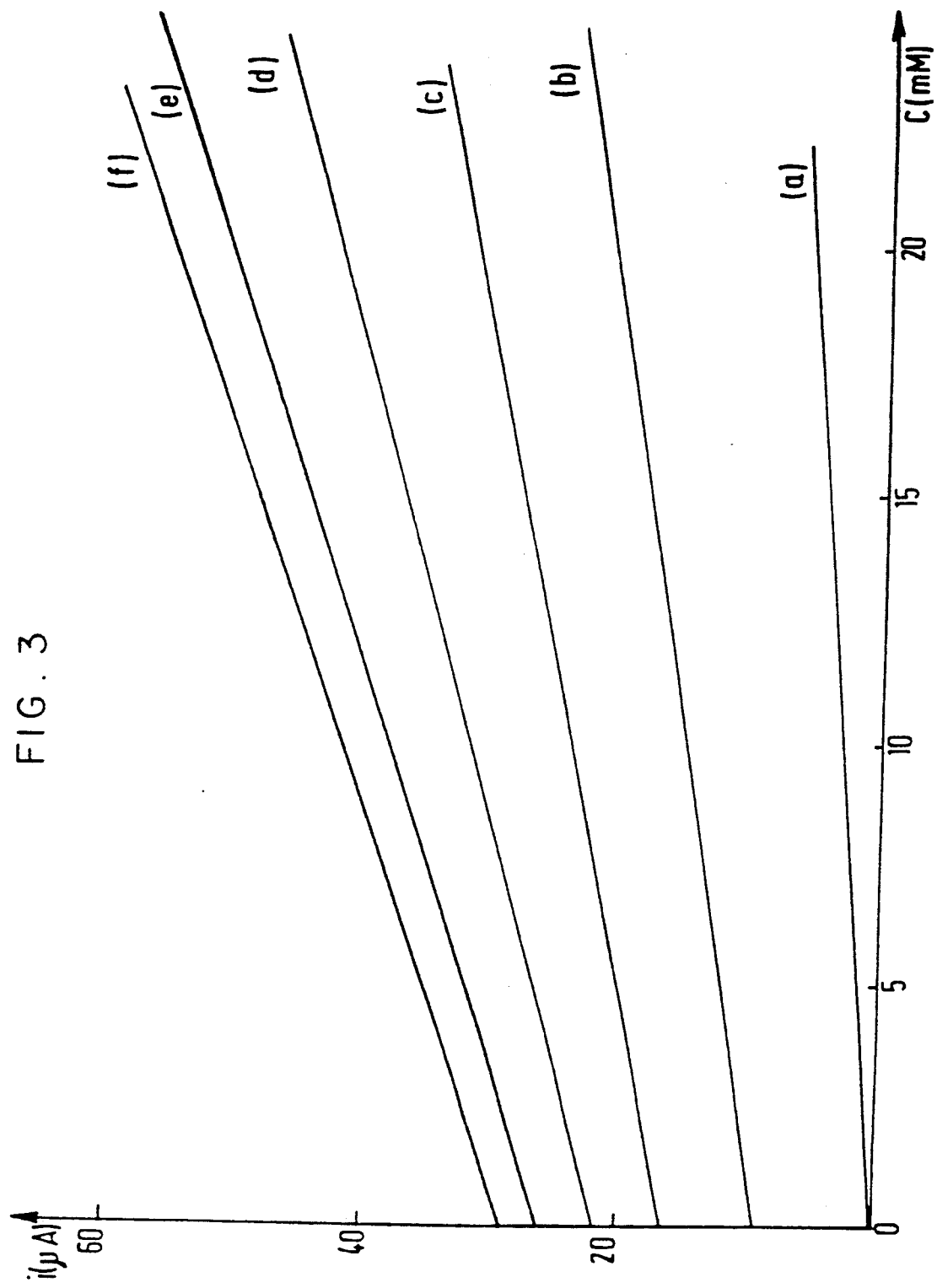

In FIG. 3 the response curves i=f(C) of this electrode as a function of the mediator concentration have been plotted for various glucose concentrations under the following conditions:

GOD concentration in the paste: 1.5% by weight ($10^3$ U per gram of paste)
*pH*: 8.8
scanning speed: 2 *mV/s*

| Legend for FIG. 3 |  |
| --- | --- |
| Abscissas: mediator concentration in the analysis medium in mM |  |
| Ordinates: current intensity in $\mu A$ |  |
| Curve | Glucose concentration in $10^{-3}$ M |
| (a) | 0 |
| (b) | 6 |
| (c) | 12 |
| (d) | 18 |
| (e) | 21 |
| (f) | 30 |

FIG. 3 shows that the sensitivity of the signal is greater the higher the mediator concentration in the solution.

EXAMPLE 2

Determination of glucose with the aid of a carbon paste electrode containing glucose oxidase and p-ferrocenylaniline as mediator.

(a) Preparation of the electrode

A chosen amount of p-ferrocenylaniline ($C_5H_5$)Fe($C_5H_4$—$C_6H_4$—$NH_2$) is dissolved in methylene chloride and a specified amount of carbon powder, analogous to that of Example 1, is added to the solution obtained. The methylene chloride is evaporated off while stirring the mixture. After complete evaporation of the solvent, a carbon powder containing the mediator in a homogeneous manner is obtained.

Two methods can be used to prepare the paste serving as the electrode:

(a) 1 g of this powder is mixed with 0.36 ml of paraffin oil until a homogeneous paste is obtained and 300 mg of the carbon paste thus obtained are then mixed intimately with 300 mg of the paste containing GOD prepared according to Example 1.

(b) A powder containing the enzyme is prepared by mixing, for example, 1 g of carbon powder with 1 ml of the crosslinking solution containing the enzyme according to Example 1 and this mixture is left at 4° C. for 10 to 30 minutes and is then scratched until a fine powder is obtained. The paste for the electrode is then prepared by mixing, for example, 1 g of this powder with 1 g of the powder containing the mediator and 0.72 ml of paraffin oil.

(b) Determination of glucose

The reactions involved are analogous to those indicated in Example 1. The analysis medium is a phosphate buffer medium of pH$\approx$8.8.

Figure 4B:
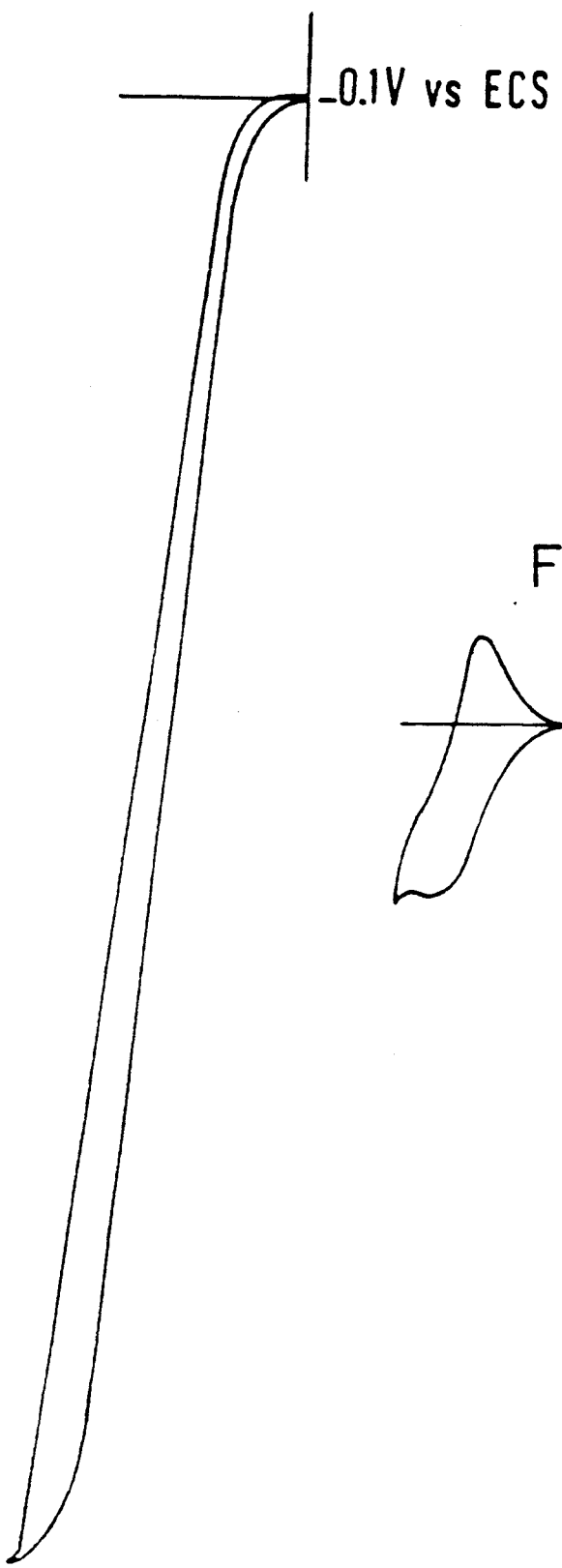
Figure 4A:
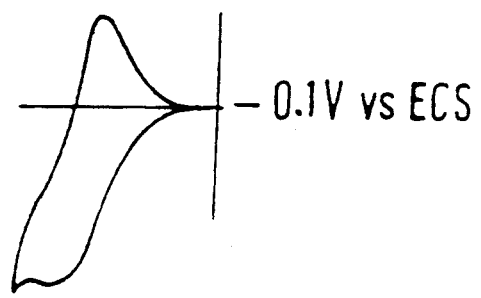

FIG. 4(*a*) shows the shape of the signal obtained i=f(E), by cyclic voltammetry, in the above-mentioned buffer medium and in the absence of glucose, with the electrode containing GOD and the mediator. FIG. 4(*b*) shows this same signal after addition of glucose.

Figure 5:
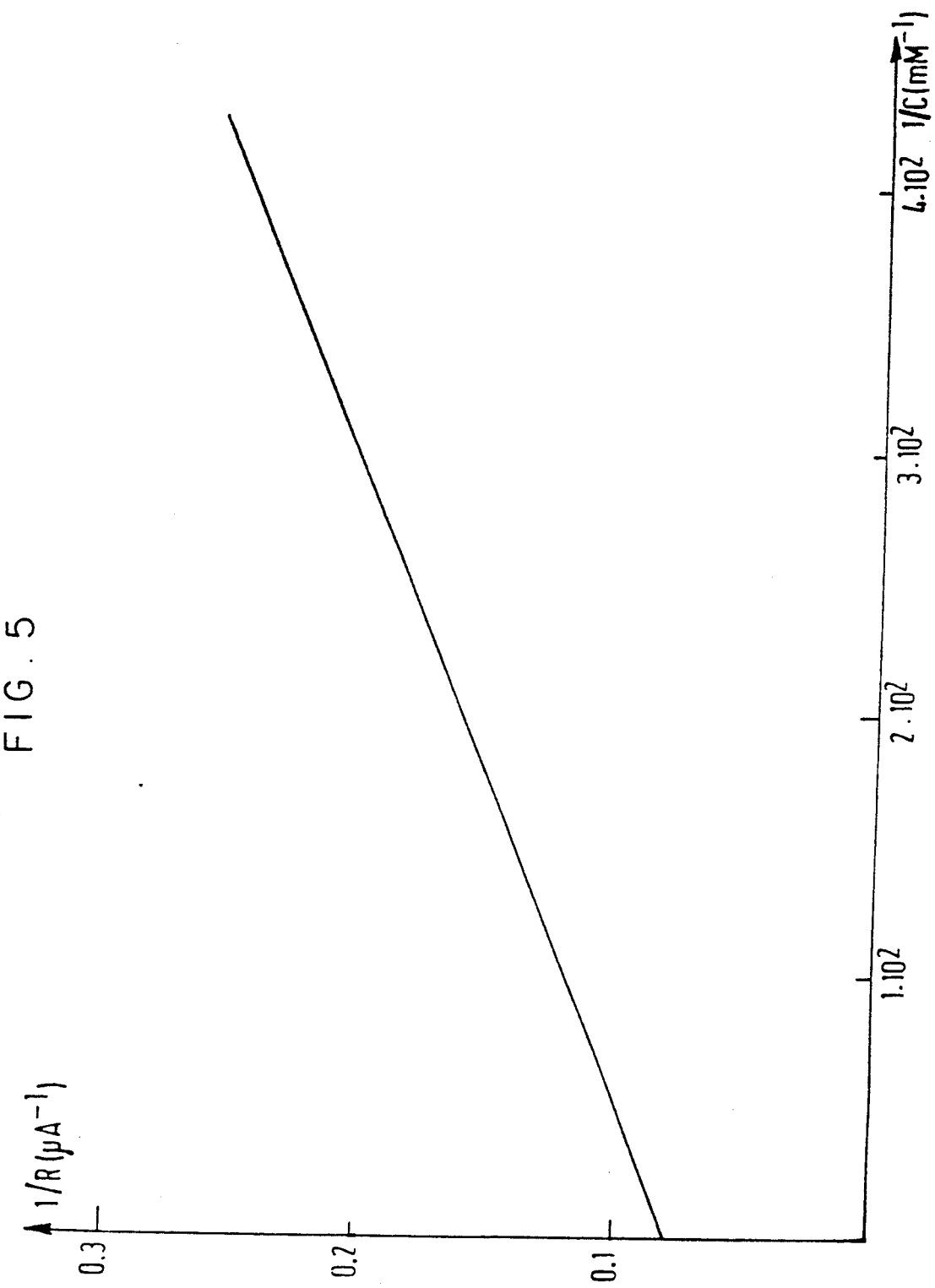

In FIG. 5 the curve $1/R=f(1/C)$ has been plotted, R being being (sic) the ratio of the signal obtained in the presence of glucose to that obtained in the absence of glucose and C the glucose concentration expressed in mM. The conditions were as follows:
amount of mediator in the paste: 0.4%;
amount of GOD in the paste: $7.10^3$ U/g;
scanning speed: 2 *mV/s*

A linear correlation is obtained between 1/R and 1/C.

Linear relationships between 1/R and 1/C were also obtained by varying the concentration of the mediator and that of the enzyme in the electrode.

Figure 6:
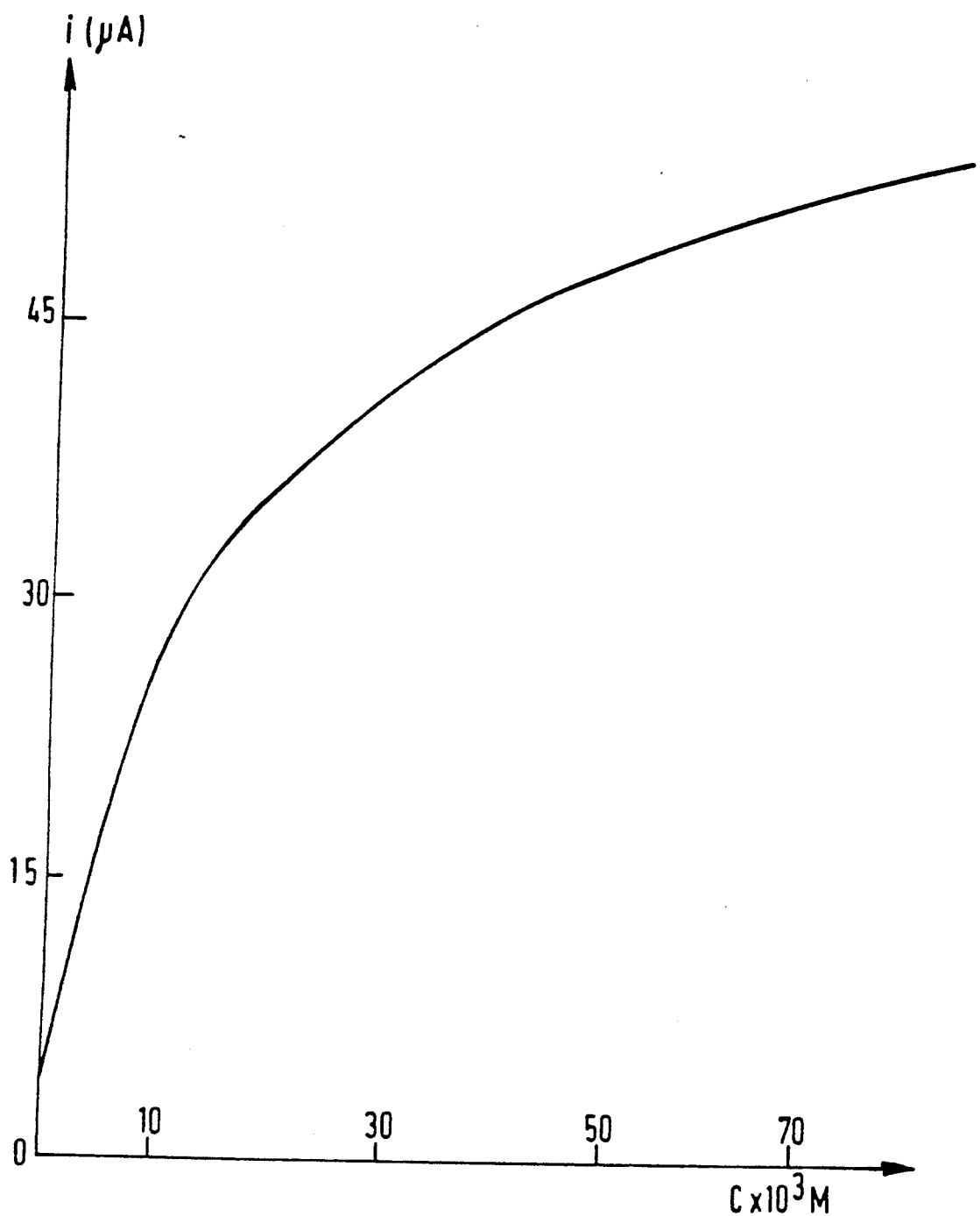
Figure 7:
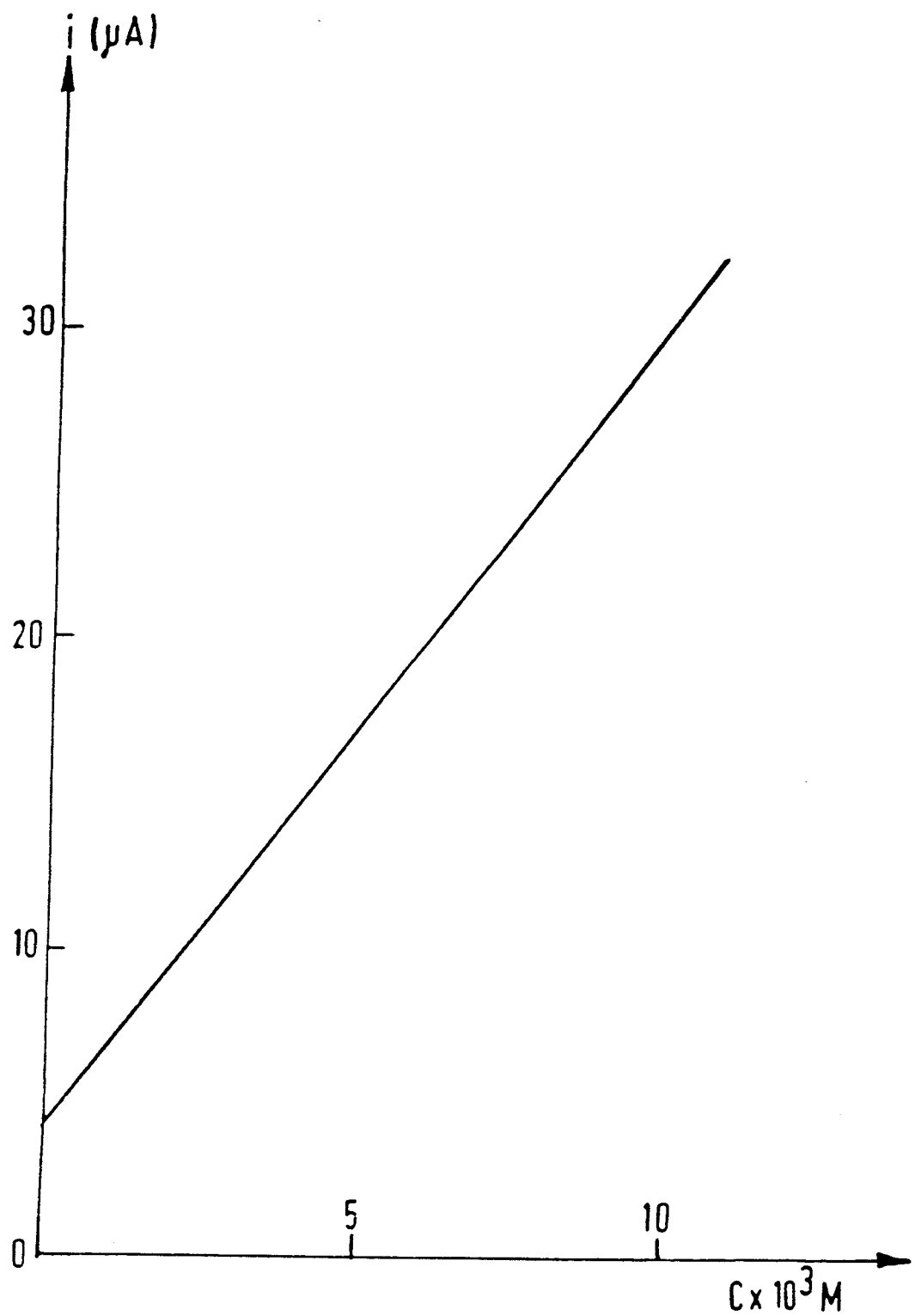

In FIG. 6 the curve which relates the amplitude of the signal i in $\mu A$ to the concentration, in mmole, of glucose in the solution has been plotted. In FIG. 7 the straight line part of this curve, that is to say for glucose concentrations equal to or less than $10.^{-2}$ mole.$1^{-1}$, has been plotted.

The conditions in these two cases were as follows:
amount of mediator in the paste: 0.46%;
amount of GOD in the paste: $5.15 \cdot 10^3$ U/g;
scanning speed: 2 *mV/s*
0.1 M phosphate buffer solution; pH$\approx$7

Figure 8:
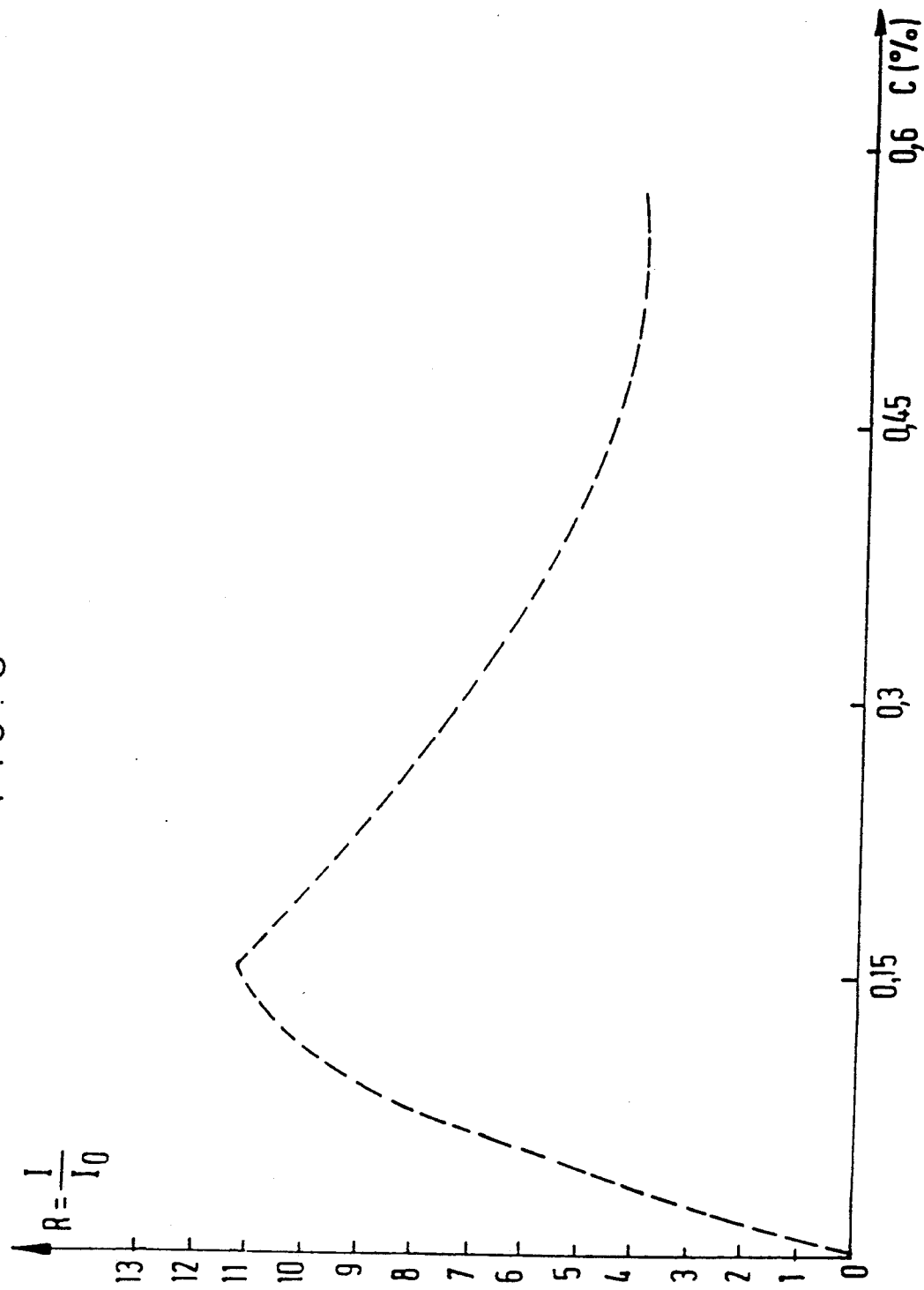

In FIG. 8 the curve representing the variation in R as a function of the mediator concentration (expressed as percent relative to the paste as a whole) has been plotted. The conditions were as follows:
glucose concentration in the analysis medium: $20 \times 10^{-3} M$
GOD concentration in the electrode: 2.9% (which is $6.25 \times 10^3$ U/g)
pH=8.9
scanning speed: 2 *mV/s*

This curve shows that although a significant signal is detected at all mediator concentrations (between 0 and 0.6%) this signal passes through a maximum at concentrations located around 0.15%.

Figure 9:
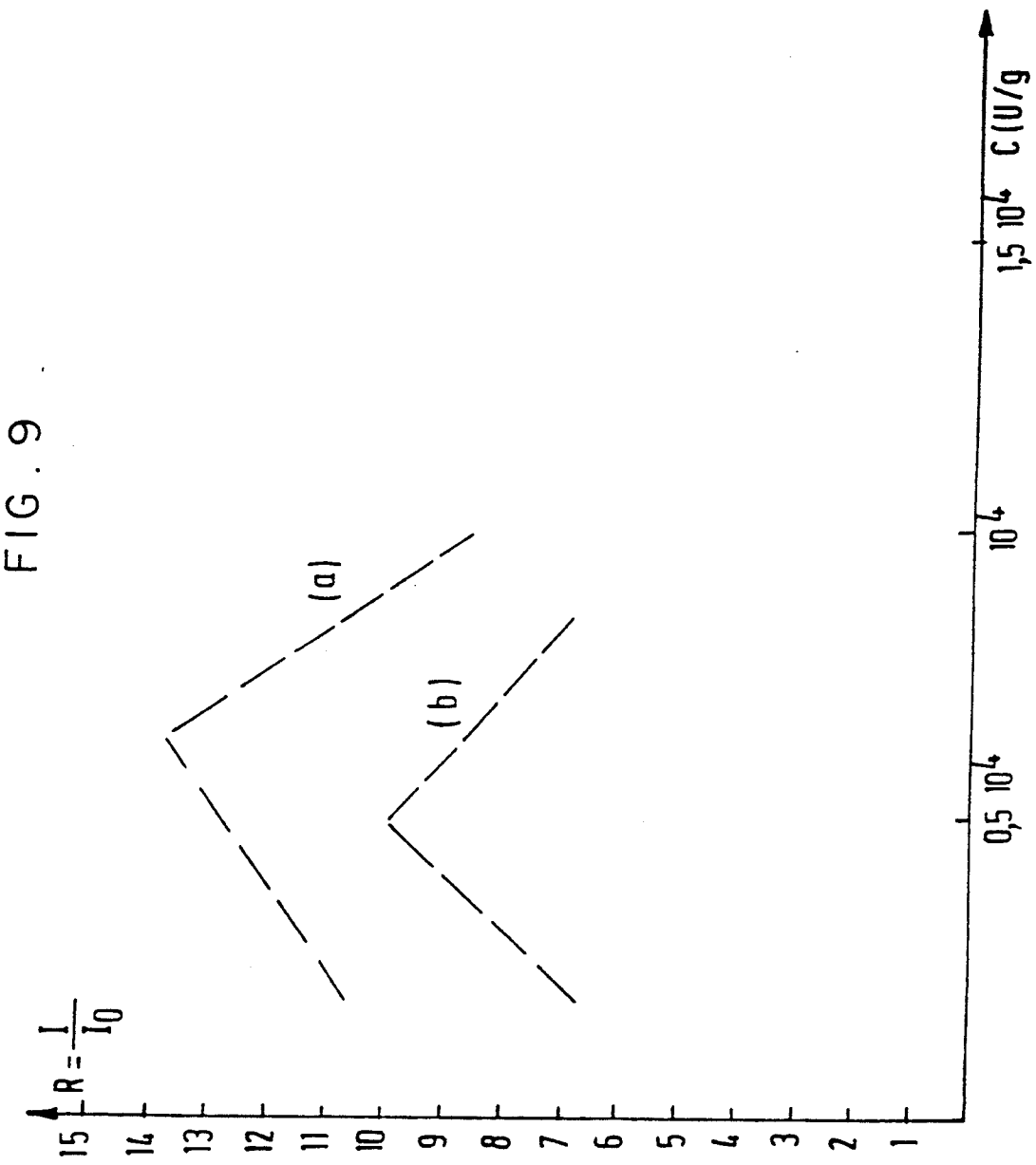

In FIG. 9, the curve representing the variation in R as a function of the GOD concentration in the electrode (expressed as U GOD/g of paste) has been plotted for mediator concentrations of 0.15 and 0.2% (curves a and b respectively) relative to the paste as a whole, under the following conditions:
glucose concentration fixed at $20 \times 10^{-3} M$;
pH$\approx$8,9;
scanning speed: 2 *mV/s*.

It is also observed here that an optimum signal is obtained when the electrode contains about $5 \times 10^3$ Units of GOD/g. However, the signal always remains significant and utilizable for concentrations either side of this value.

EXAMPLE 3

Determination of galactose with the aid of a carbon paste electrode containing galactose oxidase and p-ferrocenylaniline.

(a) Preparation of the electrode

The procedure is as in Example 2(*a*), replacing the GOD by galactose oxidase.

(b) Determination of qalactose

Figure 10A:
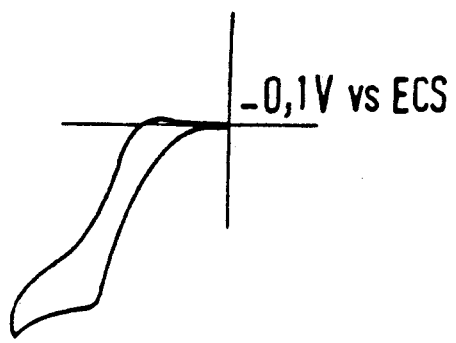
Figure 10B:
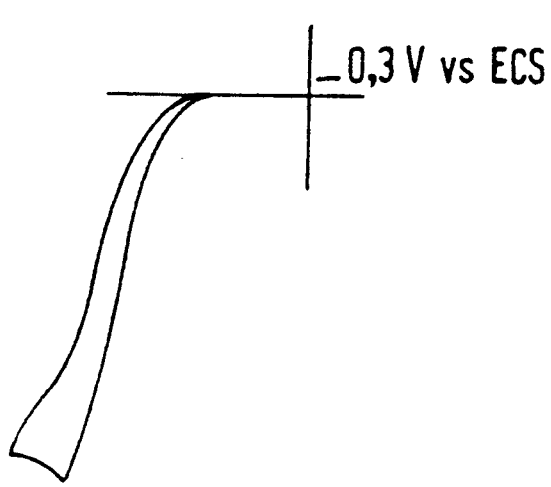

FIG. 10(*a*) shows the shape of the signal obtained by cyclic voltammetry i=f(E) with this electrode in a phosphate buffer medium of pH$\approx$8.9, in the absence of galactose, and FIG. 10(*b*) shows this same signal after the addition of galactose.

EXAMPLE 4

Determination of L-leucine with the aid of a carbon paste electrode containing L-amino acid oxidase and p-ferrocenylaniline.

(a) Preparation of the electrode

The procedure is as in Example 2(*a*), replacing the GOD by L-amino acid oxidase.

(b) Determination of L-leucine

Figure 11A:
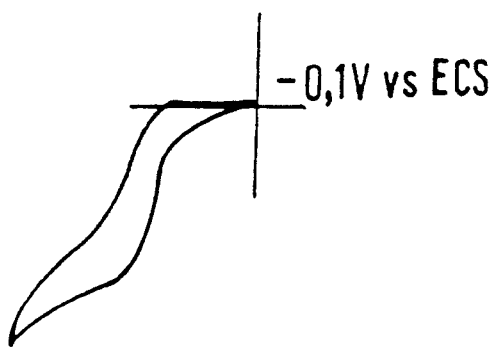
Figure 11B:
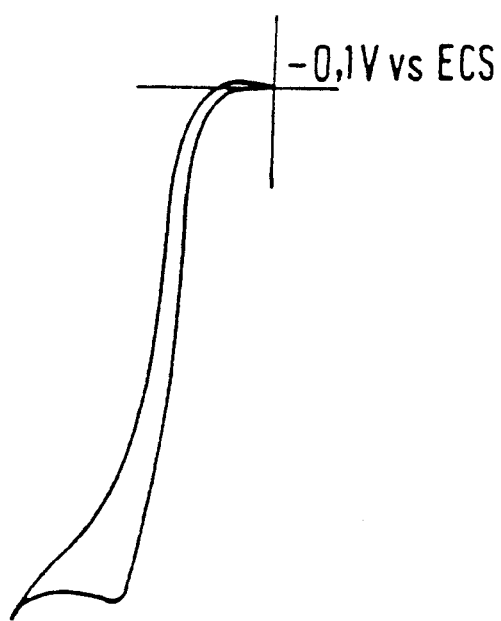

FIG. 11(a) shows the shape of the signal obtained with this electrode in a phosphate buffer medium of pH≈8.9, in the absence of L-leucine, and FIG. 11(b) shows the effect of the addition of L-leucine.

EXAMPLE 5

Determination of glucose with the aid of a carbon paste electrode containing glucose oxidase and nickelocene.

(a) Preparation of the electrode

The procedure is as in Example 2(a), replacing p-ferrocenylaniline by nickelocene: $(C_5H_5)_2Ni$.

(b) Determination of glucose

FIG. 12 shows the signal obtained with this electrode in a phosphae buffer medium of pH≈8.9 in the absence of glucose (curve a) and after addition of addition of glucose (curve b).

EXAMPLE 6

Determination of glucose with the aid of a carbon paste electrode containing glucose oxidase and bensqoquinone.

Preparation of the electrode

The procedure is as in Example 2(a), replacing p-ferrocenylaniline by benzoquinone.

(b) Determination of glucose

FIG. 13 shows the shape of the signal obtained with this electrode in a phosphate buffer medium of pH≈8.9, in the absence of glucose (curve a) and after addition of glucose (curve b).

EXAMPLE 7

Determination of sucrose with the aid of a carbon paste electrode containing invertase and glucose oxidase, and ferrocene monocarboxylic acid as mediator in solution.

(a) Preparation of the electrode

The procedure is as in Example 1, using 20 mg of GOD/(6300 U/g of paste) (sic) and 20 mg of invertase (24,000 U/g of paste), the total amount of carbon powder being 300 mg.

(b) Determination of sucrose

FIG. 14 shows the shape of the signal obtained with this electrode in a phosphate buffer medium of pH≈8.9, in the absence of sucrose (curve a) and after addition of sucrose (curve b).

Figure 15:
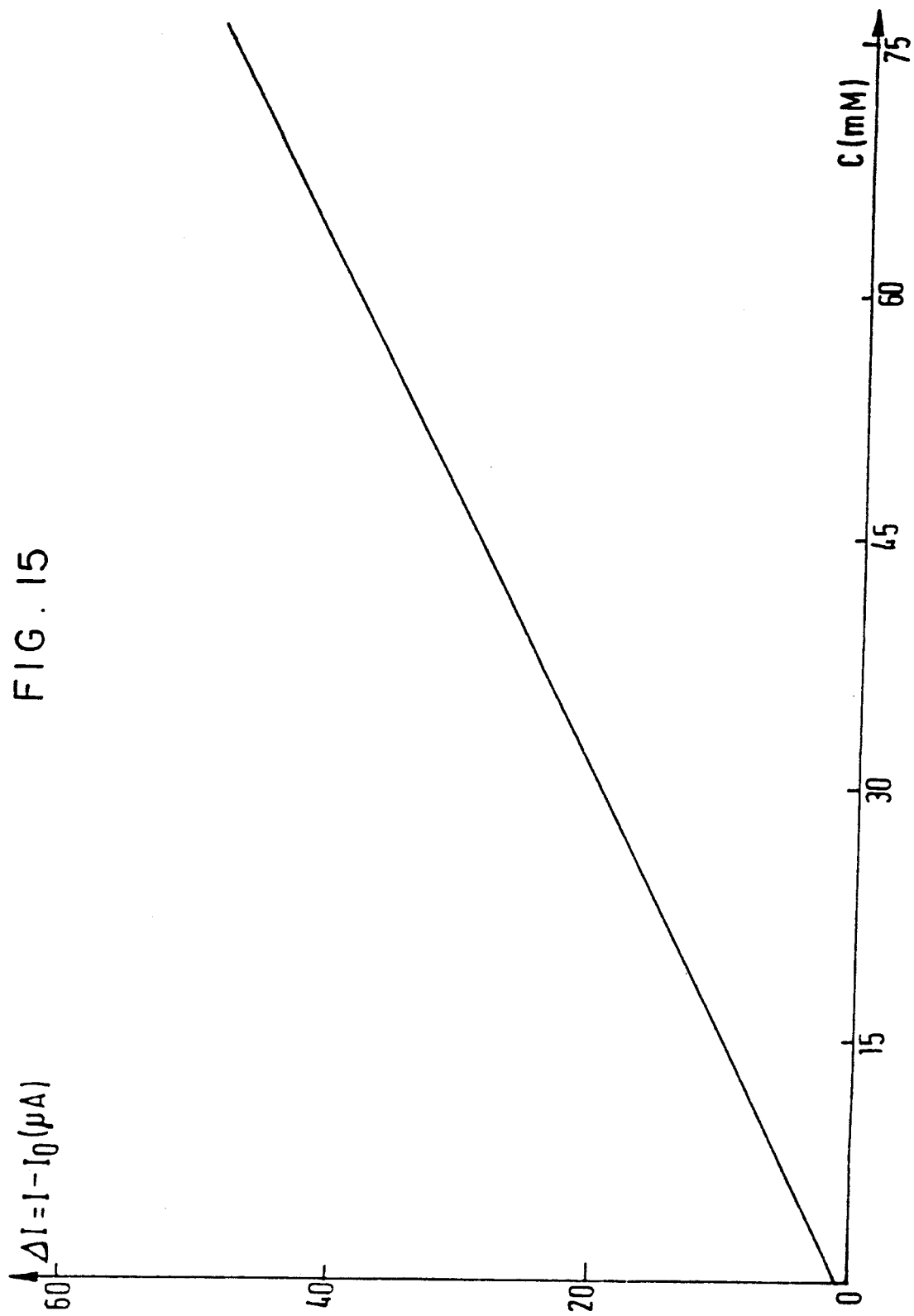

In FIG. 15 the variations in $I - I_o$ as a function of the sucrose concentration (expressed as mM) have been plotted under the following conditions:

phosphate buffer medium of pH≈8.9;
scanning speed: 2 mV/s

The relationship between the signal and the sucrose concentration is a straight line relationship.

EXAMPLE 8

Determination of sucrose with the aid of a carbon paste electrode containing invertase, glucose oxidase and p-ferrocenylaniline.

(a) Preparation of the electrode The procedure is as in Example 2, with the following concentrations:

GOD: 300 U/g of paste
invertase: 28,000 U/g of paste
p-ferrocenylaniline: 0.1% by weight of paste.

(b) Determination of sucrose

Figure 16A:
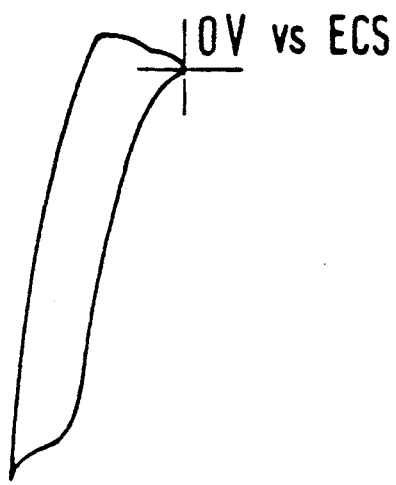
Figure 16B:
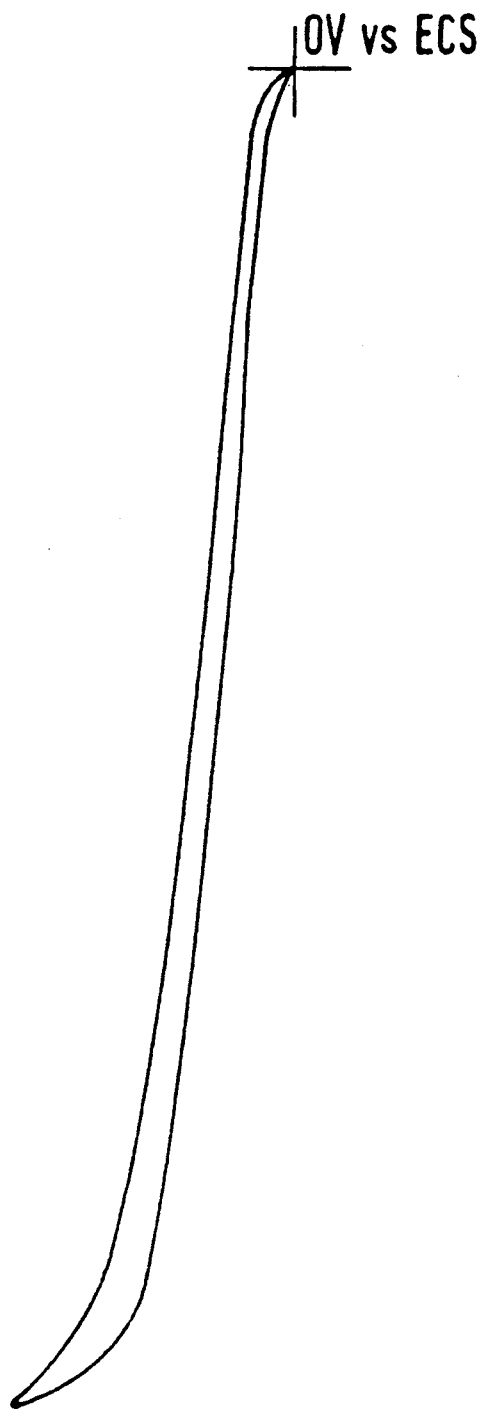

FIG. 16 shows the shape of the signal obtained with this electrode in a phosphate buffer medium of pH≈8.9, in the absence of sucrose (curve a) and after addition of sucrose (curve b).

Figure 17:
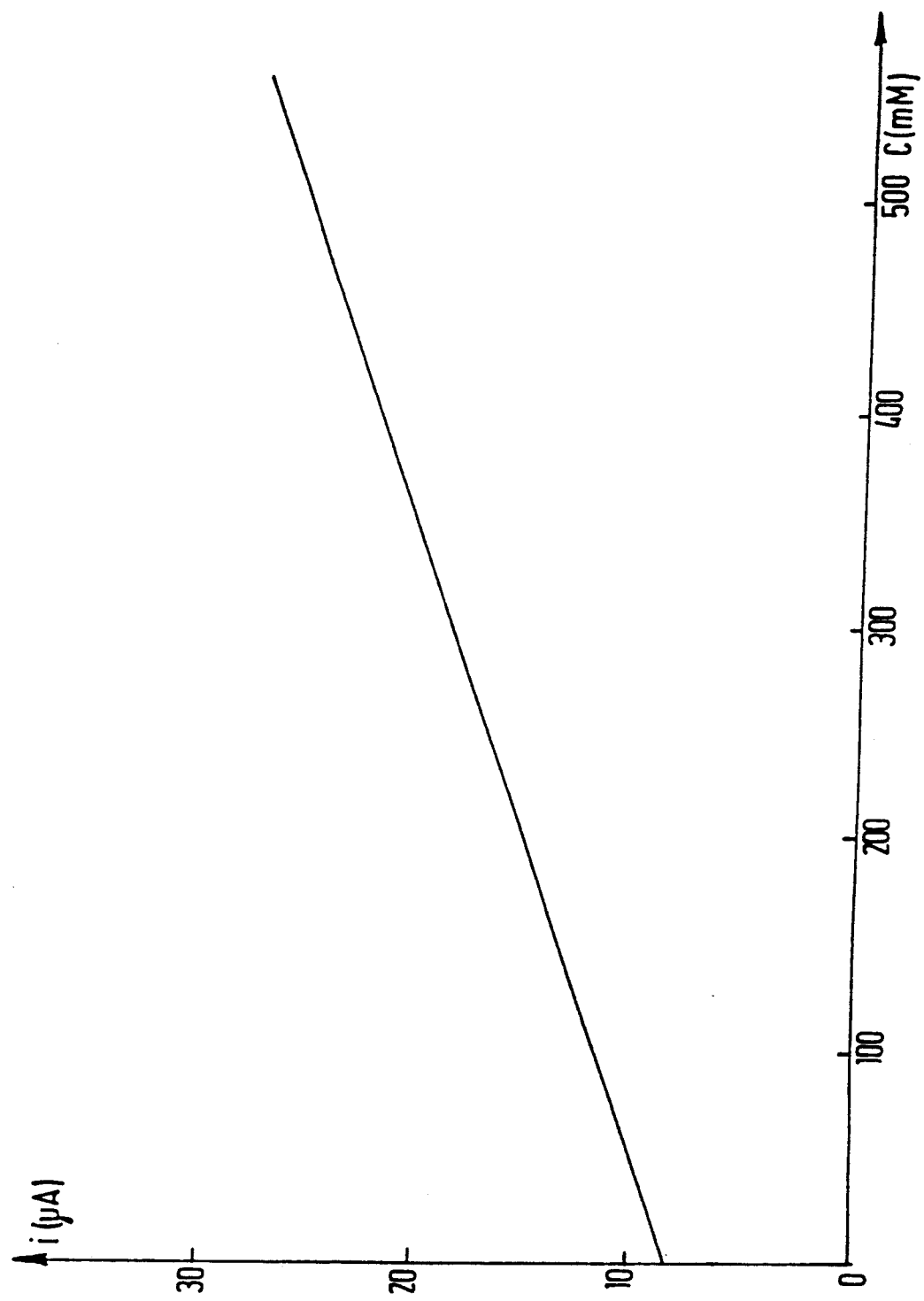

In FIG. 17 the variations in I as a function of the sucrose concentration (expressed as mM) have been plotted under the following conditions:

phosphate buffer medium of pH≈8.9;
scanning speed: 2 mV/s

The relationship between the signal and the sucrose concentration is a straight line relationship.

The determination of sucrose can advantageously be carried out with the aid of a three-enzyme electrode by incorporating, into the paste described under (a), mutarotase which will have the role of shifting the equilibrium existing between the α and β anomers of glucose (formed owing to the invertase) in favor of the β anomer, which will then be detected directly by the electrode. A three-enzyme electrode of this type then has a stronger signal than that given by the two-enzyme electrode and thus enables very low sucrose concentrations to be detected.

EXAMPLE 9

Determination of ethanol with the aid of a carbon paste electrode containing alcohol dehydrogenase and AND.

(a) Preparation of the electrode

The electrode is prepared as in Example 2(a), except that $AND^+$ replaces the mediator, the chosen amount of $AND^+$ being dissolved in water and then added to the carbon powder.

(b) Determination of ethanol

Figure 18B:
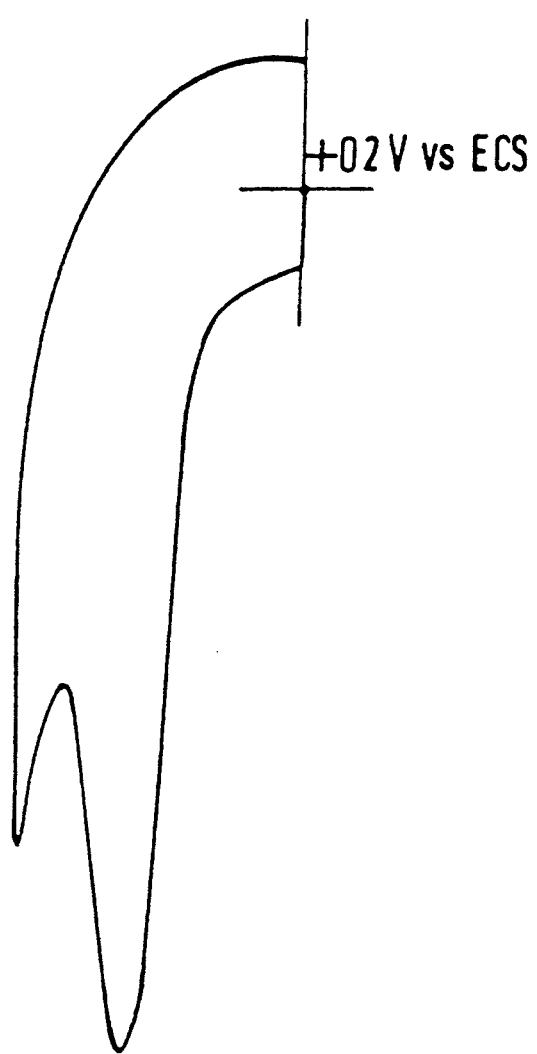
Figure 18A:
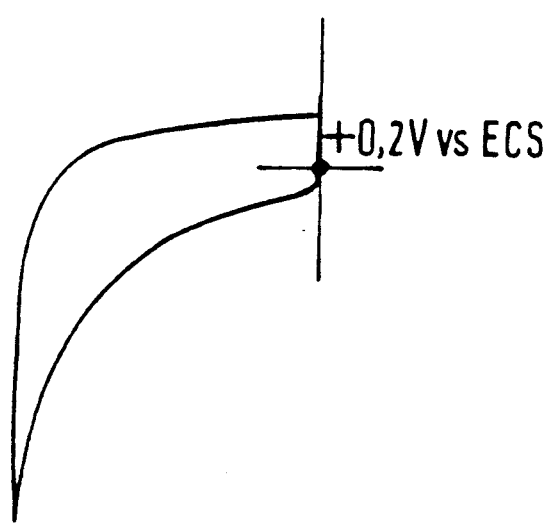

FIG. 18 shows the signal obtained with this electrode in a phosphate buffer medium of pH≈8.9, in the absence of ethanol (curve a) and after addition of ethanol (curve b).

In FIG. 19 the curve representing the variation in I as a function of the concentration (v/v) of ethanol/water has been plotted. The conditions are as follows:

phosphate buffer medium of pH≈8.9
scanning speed 50 mV/s

The relationship is a straight line relationship.

The enzymatic electrode according to the invention can be used in all fields employing enzymatic reactions, drawing benefit from their selectivity, for example for determinations in the chemical industry, in the medical and biological fields and in the agro-food-stuffs industries.

We claim:

1. An enzymatic electrode in the form of a matrix comprising a substantially homogenous admixture of a conducting powder and a member selected from the group consisting of (a) at least one immobilized enzyme, (b) an immobilized enzyme and a mediator agent and (c) an immobilized enzyme and a co-enzyme, wherein neither the mediator agent nor the co-enzyme is cross-linked to the matrix.

2. An enzymatic electrode of claim 1 having an intimately combined enzymatic part and detection part said electrode having a surface available for direct contact with a substrate without a permeable or semi-permeable intermediate membrane or membranes.

3. Electrode according to claim 2, which is constructed and adaptable is of the disposable, once-only use, type.

4. An electrode according to claim 2, wherein the conducting powder is carbon powder or graphite powder.

5. An electrode according to claim 2, wherein the conducting powder is capable of forming a matrix and physically, confining the enzyme.

6. An electrode according to claim 2, which contains several enzymes immobilized in the matrix.

7. An electrode according to claim 2, wherein the matrix is contained in an inert sheath, from which it protrudes at one end to form the surface, which is the useful surface of the electrode.

8. An electrode according to claim 2, for the determination of glucose, wherein the immobilized enzyme is glucose oxidase and the conducting matrix also contains a mediator selected from the group consisting of p-ferrocenylaniline, nickelocene and benzoquinone.

9. An electrode according to claim 2, for the determination of sucrose, wherein the at least one immobilized enzyme is invertase and glucose oxidase, or invertase, glucose oxidase and mutarotase.

10. An electrode according to claim 2, for the determination of ethanol, wherein the immobilized enzyme alcohol dehydrogenase, which is combined with $NAD^+$.

11. An electrode according to claim 1 constructed and adapted to have a defined surface area for contacting the substrate, the surface area being one which is removable friction or cutting means to expose another surface having the identical surface area.

12. An electrode according to claim 1 wherein the mediator agent is a member selected from the group consisting of ferrocene, a ferrocene derivative, nickelocene, a nickelocene derivative and benzoquinone.

13. An electrode according to claim 2, wherein the enzyme is fixed within the matrix of conducting material by means of at least one crosslinking agent.

14. An electrode according to claim 13, wherein the crosslinking agent is glutaraldehyde.

15. An electrode according to claim 1 wherein the matrix comprises a conducting paste which is an intimate mixture of the powder with from 10 to 40% by weight of inert binder relative to the weight of the conducting paste.

16. An electrode according to claim 15, wherein the binder is a hydrophobic binder.

17. An electrode according to claim 16, wherein the binder consists of paraffin oil, alpha-bromo-naphthalene or a silicone oil.

18. A process for the preparation of an enzymatic electrode as defined in claim 2 which comprises intimately mixing
   a homogeneous paste or matrix resulting from the intimate admixture of a conducting powder with a binder;
   at least one enzyme; and
   an enzyme crosslinking solution;
   and then incorporating a mediator agent and/or a co-enzyme therein.

19. A process according to claim 18, wherein a conducting powder capable of forming a matrix and at least one enzyme are intimately mixed with a mediator agent and/or a co-enzyme and the resulting mixture is subjected to mechanical forces, in order to obtain a solid matrix physically confirming the immobilized enzyme.

20. A process according to claim 19, wherein the mechanical forces are compression forces.

* * * * *